United States Patent [19]

Lee

[11] 4,298,760

[45] Nov. 3, 1981

[54] PROCESS FOR PREPARING 1-AMINOCYCLOPROPANE-1-CARBOXYLIC ACID

[75] Inventor: Shy-Fuh Lee, Sunnyvale, Calif.

[73] Assignee: Zoecon Corporation, Palo Alto, Calif.

[21] Appl. No.: 178,062

[22] Filed: Aug. 14, 1980

[51] Int. Cl.³ .............................................. C07C 51/09
[52] U.S. Cl. .............................. 562/506; 260/465 D; 560/35
[58] Field of Search ........................................ 562/506

[56] References Cited

PUBLICATIONS

Schollkopf, Chem. Ber., 108, pp. 1580–1592, (1975).

Primary Examiner—Natalie Trousof
Assistant Examiner—Michael Shippen
Attorney, Agent, or Firm—Donald W. Erickson; Jacqueline S. Larson

[57] ABSTRACT

An improved process for preparing 1-aminocyclopropane-1-carboxylic acid, which acid is a plant growth regulator.

4 Claims, No Drawings

PROCESS FOR PREPARING 1-AMINOCYCLOPROPANE-1-CARBOXYLIC ACID

This invention relates to an improved process for the preparation of 1-aminocyclopropane-1-carboxylic acid.

1-Aminocyclopropane-1-carboxylic acid (ACPCA) is a naturally occurring plant hormone which regulates many aspects of plant growth and development. Derivatives of 1-aminocyclopropane-1-carboxylic acid have been claimed as plant growth regulators (West German DT No. 28 24 517).

Unfortunately, preparative methods of ACPCA up to this time have required several reaction steps, have produced a low yield of the product, and have been uneconomical. Such multi-step processes are described by I. Bregovec and T. Jakovic, *Manatsh. Chem.* 103, 288 (1972); by D. H. Rich and J. P. Tam, *Synthesis*, 46 (1978); and by U. Schöllkopf et al., *Liebigs Ann. Chem.*, 611 (1973). In contrast, the process of the present invention is simple, requiring only two steps, with a corresponding high yield of ACPCA.

The process of the present invention can be illustrated as follows:

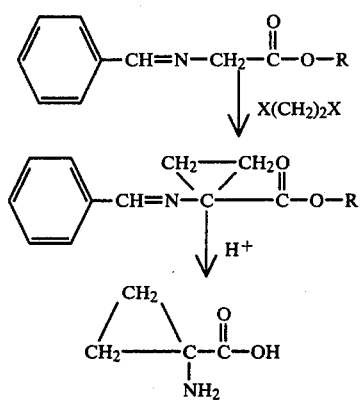

In the above formulas, R is lower alkyl, aryl or substituted aryl; and X is bromo, chloro or iodo.

In the practice of the above-outlined synthesis, the ester of formula (1) is reacted with at least one molar equivalent of $X(CH_2)_2X$ in the presence of at least two molar equivalents of a base, such as lithium diisopropylamide or triethylbenzyl ammonium hydroxide, and a solvent suitable for the base used, at room temperature or below, to give the cyclopropyl ester of formula (2). Compound (2) is hydrolyzed with a strong acid, such as hydrochloric or sulfuric acid, to yield the acid salt of 1-aminocyclopropane-1-carboxylic acid, which is then converted to the free compound by such means as passing through an ion exchange resin.

The following terms, wherever used in the description herein and in the appended claims, have the meaning defined below, unless otherwise specified hereinafter.

The term "lower alkyl" refers to an alkyl group, straight or branched, having a chain length of one to six carbon atoms.

The term "aryl" refers to the aryl group phenyl or naphthyl. The term "substituted aryl" refers to an aryl group substituted at one, two or three of the ring carbon atoms with a group selected from lower alkyl, lower haloalkyl, halogen, nitro, cyano, hydroxy, and the like.

The following examples are provided to illustrate the practice of the present invention. RT means room temperature. Temperature is given in degrees Centigrade.

EXAMPLE 1

To a solution of 21.9 ml of diisopropylamine in 300 ml of tetrahydrofuran, under nitrogen at 0°, is added dropwise 180 ml of 1.6 M n-butyllithium is hexane. The solution is stirred at 0° for 20 minutes, then cooled to −78°. Anhydrous hexamethylphosphoramide (55 ml) is added dropwise, followed by 20 g of benzylidene glycine ethylester in 10 ml tetrahydrofuran. The reaction mixture is stirred at −78° for 10 minutes, after which 45 ml of 1,2-dibromoethane is added. The mixture is stirred at −78° for 8 hours, then at RT for 24 hours. This is then concentrated at 40°. The oily residue is neutralized with saturated aqueous ammonium chloride and extracted with ether. The ether extracts are washed, dried and evaporated to dryness. The hexamethylphosphoramide is removed under vacuum at 120° to yield benzylidene cyclopropyl ethyl ester.

Benzylidene cyclopropyl ethyl ester (18.9 g) in 250 ml of 6 N hydrochloric acid is refluxed for 24 hours. Water is then removed under reduced pressure, and the amino salt is passed through ion-exchange resin (Amberlite IR-4B). The aqueous solution is freeze-dried to give 1-aminocyclopropane-1-carboxylic acid.

EXAMPLE 2

Following the procedure of Example 1, benzylidene glycine phenyl ester is reacted with 1,2-dichloroethane to give benzylidene cyclopropyl phenyl ester, which is then hydrolyzed to yield 1-aminocyclopropane-1-carboxylic acid.

Benzylidene glycine phenyl ester can be made by reaction of glycine phenyl ester hydrochloride (107 mmol) with benzaldehyde (72 mmol) in the presence of triethylamine (30 ml), magnesium sulfate (8 g) and dichloromethane, under nitrogen and with stirring at RT for about 24 hours. The mixture is filtrated and the filtrate is concentrated. The residue is taken up in ether, washed with brine and evaporated to dryness to give benzylidene glycine phenyl ester.

What is claimed is:

1. A process for the preparation of the compound 1-aminocyclopropane-1-carboxylic acid which comprises the steps:

(a) of reacting a compound of the formula

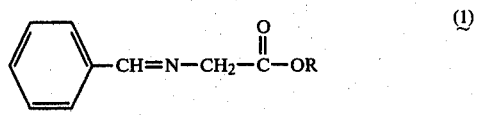

wherein R is lower alkyl, unsubstituted aryl or aryl substituted at one, two or three of the ring carbon atoms with a group selected from lower alkyl, lower haloalkyl, halogen, nitro, cyano or hydroxy, with the compound $X(CH_2)_2X$ wherein X is bromo, chloro or iodo, in the presence of a base to produce a compound of the formula

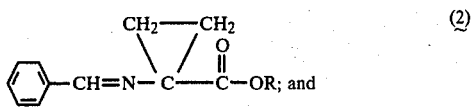

(b) hydrolyzing said compound (2) to prepare 1-aminocyclopropane-1-carboxylic acid.

2. A process according to claim 1 wherein R is lower alkyl.

3. A process according to claim 2 wherein R is methyl or ethyl.

4. A process according to claim 1 wherein the reaction of step (a) is carried out at room temperature or below.

* * * * *